United States Patent [19]

Papa et al.

[11] Patent Number: 4,945,185
[45] Date of Patent: Jul. 31, 1990

[54] PROCESS FOR PRODUCING MIXTURES OF KETONES AND ALDEHYDES

[75] Inventors: Anthony J. Papa, St. Albans; David R. Bryant, S. Charleston, both of W. Va.

[73] Assignee: Union Carbide Chemicals and Plastics Company Inc., Danbury, Conn.

[21] Appl. No.: 445,927

[22] Filed: Dec. 5, 1989

Related U.S. Application Data

[63] Continuation of Ser. No. 137,670, Dec. 24, 1987, abandoned.

[51] Int. Cl.$^5$ .............................................. C07C 45/49
[52] U.S. Cl. .................................. 568/387; 568/451; 568/454
[58] Field of Search .......................... 568/387, 451, 454

[56] References Cited

U.S. PATENT DOCUMENTS

| | | | |
|---|---|---|---|
| 2,699,453 | 1/1955 | Naragon et al. | 260/597 |
| 3,555,098 | 1/1971 | Olivier et al. | 260/604 |
| 3,829,499 | 8/1974 | Nozaki | 260/597 A |
| 3,857,893 | 12/1974 | Nozaki | 260/597 A |
| 3,917,677 | 11/1975 | Moris | 260/497 A |
| 3,923,904 | 12/1975 | Hara | 260/597 A |
| 3,959,385 | 5/1976 | Nienburg et al. | 260/604 HF |
| 3,992,451 | 11/1976 | Schmerling | 568/387 |
| 4,244,255 | 9/1980 | Smith | 568/451 |
| 4,400,549 | 8/1983 | Richter et al. | 568/454 |
| 4,593,126 | 6/1986 | Cornils et al. | 568/387 |
| 4,740,626 | 4/1988 | Bahrmann et al. | 568/454 |

FOREIGN PATENT DOCUMENTS

| | | | |
|---|---|---|---|
| 1793320 | 3/1972 | Fed. Rep. of Germany | 568/454 |
| 49-048406 | 12/1974 | Japan | 568/454 |
| 56-049333 | 3/1981 | Japan | 568/454 |
| 813903 | 10/1983 | U.S.S.R. | 568/454 |
| 1181806 | 2/1970 | United Kingdom | 568/454 |
| 2185740 | 7/1987 | United Kingdom | 568/387 |

OTHER PUBLICATIONS

"Rhodium-Catalyzed Low Pressure Hydroformylation of Vinyl Esters: Solvent and Phosphine Effects on Catalyst Activity, Selectivity and Stability", by A. G. Abatjoglou et al., *Journal of Molecular Catalysts*, vol. 18, (1983), pp. 381 to 390.

*Primary Examiner*—James H. Reamer
*Attorney, Agent, or Firm*—Reynold J. Finnegan

[57] ABSTRACT

A hydrocarbonylation process for producing an aldehyde or a mixture of a ketone and an aldehyde which comprises:
(I) forming a reaction mixture comprising:
  (a) a catalytic amount of a complex catalyst consisting essentially of rhodium in complex combination with:
    (i) a triorganophosphine, and
    (ii) a carboxylic acid having a phenyl group substituted at the para position with a non-reactive electron-withdrawing group, said phenyl group being free of further substitution and said electron withdrawing group being substantially non-reactive in said process;
  (b) an alpha-olefin having 2 to 5 carbon atoms,
  (c) carbon monixide, and
  (d) hydrogen
with the proviso that the reaction mixture has mole ratio of said carbxoylic acid to rhodium of at least about 2; and
(II) maintaining the reaction mixture at a temperature and pressure at which said (b), (c) and (d) react to form an aldehyde or a mixture of an aldehyde and a ketone.

17 Claims, 3 Drawing Sheets

PROCESS FOR PRODUCING MIXTURES OF KETONES AND ALDEHYDES

This application is a continuation of prior U.S. application Ser. No. 137,670 filed Dec. 24, 1987, now abandoned.

FIELD OF THE INVENTION

This invention relates to a rhodium-catalyzed hydrocarbonylation process for producing an aldehyde or a mixture of a ketone and an aldehyde by the reaction of an alpha olefin with carbon monoxide and hydrogen, and, more particularly, to a rhodium-catalyzed process for producing an aldehyde or a mixture of a ketone and aldehyde utilizing an acid-containing catalyst having a relatively long life. Hydroacylation and hydroformylation are herein collectively referred to as "hydrocarbonylation." The term "hydroformylation" is applied to the reaction of an alpha olefin, carbon monoxide and hydrogen to produce aldehydes. The production of ketones by the reaction of an alpha-olefin, carbon monoxide and hydrogen is termed "hydroacylation." In addition to ketones, such hydroacylation processes inherently produce varying amounts of aldehyde product.

BACKGROUND OF THE INVENTION

In addition to providing an acceptable rate of reaction at relatively low pressures and temperatures, a hydrocarbonylation catalyst should provide good catalytic activity over a sufficiently long period of operation of the process to make its use economically feasible. Further, in the case of hydroacylation processes, the catalyst should also provide the degree of ketone selectivity required for a particular application. Acceptable levels of ketone selectivity are widely variable and can range from ketone yields as low as 5 weight percent of the aldehyde and ketone produced up to ketone yields of 40 weight percent or more of aldehyde and ketone produced.

British Patent No. 1,181,806 discloses a process for the production of alcohols and/or aldehydes by the reaction of an alpha olefin, carbon monoxide and hydrogen in the presence of a square planar complex of monovalent rhodium containing at least one carboxylate ligand derived from aliphatic, substituted aliphatic, aromatic or substituted aromatic carboxylic acids, with the carboxylic acids of choice being acetic, propionic, pivalic and isobutyric acids. British Patent '806 further discloses that the square planar rhodium complex may further comprise at least one trialkyl phosphine, triaryl phosphine, trialkyl arsine, triaryl arsine, trialkyl stilbine, triaryl stilbine, pyridine or amine. Preferred catalysts of this British Patent are compounds of the formula:

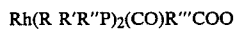

Rh(R R'R"P)$_2$(CO)R'"COO wherein R, R', R", and R'" are alkyl or aryl groups any number of which may be identical. Disclosed reaction conditions include temperatures of between 60° C. and 200° C. and pressures between 300 psig and 1,000 psig. The patent exemplifies as suitable catalysts rhodium bis (tri-n-alkyl phosphine) carbonyl carboxylates and rhodium bis-(tri-n-alkyl amine) carbonyl carboxylates, all of which have a carboxylic acid to rhodium mole ratio of 1.

The square planar compounds of this British Patent are further characterized as having a characteristic peak at 1970 cm$^{-1}$ in their infra red spectra. For comparative purposes, infra red spectra of trans- Rh (O$_2$CC$_6$H$_4$p-NO$_2$)(CO) ((C$_6$H$_5$)$_3$P)$_2$, a square planar compound having a characteristic peak at 1970 cm$^{-1}$ (Spectrum B), and an isolatable complex intermediate of the present invention, having a mole ratio of carboxylic acid to rhodium of at least about 2, (Spectrum A) are provided herein in FIG. 1. As shown by FIG. 1, Spectrum A lacks the peak at 1970 cm$^{-1}$ which is characteristic of the square planar rhodium compounds of British Patent '806. In use, the catalysts exemplified by British Patent '806 tend to become deactivated after relatively short periods of operation.

U.S. Pat. No. 4,224,255 to Smith discloses a rhodium catalyzed process for hydroformylating alpha olefins by reaction with hydrogen and carbon monoxide wherein aldehyde formation is enhanced by the addition of an acidic compound to the reaction medium to suppress olefin hydrogenation. The acid of choice in the Smith patent is o-phthalic acid. Disclosed process conditions include pressures of one atmosphere up to 10,000 psig and temperatures of 10° C. to 250° C., with preferred conditions being pressures of from about 300 psig to about 1200 psig and temperatures of from about 70° C. to about 250° C. The processes exemplified by the Smith patent generally sustain commercially unacceptable levels of rhodium deactivation after relatively short periods of operation.

British Pat. No. 1,181,806 and U.S. Pat. No. 4,224,255 notwithstanding, the presence of acids in a hydroformylation reaction medium has been disclosed as having a deleterious effect on catalyst activity. U.S. Pat. No. 3,555,098 to Oliver et al. describes a hydroformylation process employing as a catalyst, a complex of a biphyllic ligand (e.g., a triaryl phosphine) and rhodium wherein the reaction medium is treated with an aqueous alkaline wash to extract carboxylic acid by products from same. Oliver et al. disclose that unless removed, accumulated carboxylic acid by product will deactivate the catalyst, see U.S. Pat. No. 3,555,098 at column 1, lines 13 to 25; and column 1, line 64 to column 2, line 18. The deactivation of rhodium catalysts by acid by-products is also disclosed in "Rhodium Catalyzed Low Pressure Hydroformylation of Vinyl Esters: Solvent and Phosphine Effects on Catalyst Activity, Selectivity and Stability", by A. G. Abatjoglou et al., Journal of Molecular Catalysis, Vol. 18 (1983) at pp. 383 to 385.

Much of the art relating to rhodium-catalyzed hydroacylation processes suggests that the use of relatively high pressures and/or temperatures is critical to obtaining desirable ketone selectivity and/or acceptable reaction rates. For example, German Pat. No. 1,793,320 disclosing the rhodium-catalyzed reaction of ethylene, carbon monoxide and hydrogen to produce ketones, requires the use of pressures of from about 200 atmospheres to about 300 atmospheres and temperatures of from about 150° C. to about 200° C.

Although hydroacylation processes which utilize more moderate conditions of temperature and/or pressure are known in the art, such processes generally do not employ a rhodium catalyst. For example, U.S. Pat. No. 2,699,453, to Naragon et al. discloses a process for producing diethyl ketone by reacting ethylene, carbon monoxide and hydrogen in the gas phase at a mole ratio of ethylene to carbon monoxide of at least 1.5 and a mole ratio of ethylene to hydrogen of at least 0.67. The process is disclosed as being carried out at a temperature below 300° F. and at a pressure that can be relatively low (i.e., as low as about 100 pounds per square inch) in the presence of a catalyst containing a metal of the iron group. However, Naragon et al. disclose that optimum results are obtained at operating pressures of about 300 to 700 pounds per square inch in the absence of a gaseous diluent and at operating pressures of about 500 to 1400 pounds per square inch in the presence of such a diluent.

U.S. Pat. No. 3,857,893, to Nozaki discloses a hydroacylation process for producing diethyl ketone from the reaction of ethylene, carbon monoxide and hydrogen at a temperature of from about 50° C. to about 150° C. and a pressure of about 50 psig to 2,000 psig in the presence of a catalytic amount of a cobalt carbonyl complex. Operating pressures exemplified by the Nozaki patent range from 250 psig to 500 psig.

Russian Pat. No. 813,908 discloses the use of palladium catalysts in the presence of phosphines and aqueous solutions of trifluoroacetic acid to effect the hydroacylation reaction of ethylene or propylene with carbon monoxide and hydrogen to produce diethylketone or dipropylketone. Disclosed process conditions are temperatures of 30° C. to 70° C. and atmospheric pressures.

The above described hydroacylation processes are generally found to be commercially non viable in that they require the use of disadvantageously high pressures and/or temperatures, produce undesirable quantities of aldehyde product, and/or proceed at undesirably slow rates and/or, in the case of processes utilizing rhodium catalysts, the catalysts have relatively short lives.

OBJECTS OF THE INVENTION

It is an object of this invention to provide a hydrocarbonylation process for producing an aldehyde or a mixture of a ketone and an aldehyde by the reaction of an alpha olefin, carbon monoxide and hydrogen utilizing a relatively "stable" acid containing rhodium catalyst (i.e. a rhodium catalyst having good catalytic activity over a relatively long period of operation of the process).

It is a further object of this invention to provide a rhodium-catalyzed hydroacylation process operable at relatively low temperatures and pressures.

It is a further object of this invention to provide a rhodium catalyzed hydroacylation process for producing mixtures of ketones and aldehydes at commercially acceptable rates.

It is yet another object of this invention to provide a rhodium catalyzed low pressure hydroacylation process capable of selectively producing ketones in relatively large quantities.

SUMMARY OF THE INVENTION

The present invention comprises a hydrocarbonylation process for producing an aldehyde or a mixture of a ketone and an aldehyde which comprises:

(I) forming a reaction mixture comprising:
  (a) a catalytic amount of a complex catalyst consisting essentially of rhodium in complex combination with:
    (i) a triorganophosphine, and
    (ii) a carboxylic acid having a phenyl group substituted at the para position with an electron-withdrawing group, said phenyl group being free of further substitution and said electron-withdrawing group being substantially non-reactive in said process.
  (b) a alpha olefin having 2 to 5 carbon atoms inclusive,
  (c) carbon monoxide, and
  (d) hydrogen with the proviso that the reaction mixture has a mole ratio of said carboxylic acid to rhodium of at least about 2; and (II) maintaining the reaction mixture at a temperature and pressure at which said (b), (c) and (d) react to form an aldehyde or a mixture of a ketone and an aldehyde.

In another embodiment this invention relates to a process for producing a rhodium complex catalyst which comprises:

(I) forming a catalyst forming reaction mixture comprising
  (a) a rhodium source,
  (b) a triorganophosphine source,
  (c) a carboxylic acid having a phenyl group substituted at the para position with a substantially non-reactive electron-withdrawing group and free of further substitution, and
  (d) an organic compound that is a solvent for (a), (b) and (c); with the proviso that the catalyst-forming mixture is provided with a sufficient amount of said carboxylic acid to provide said catalyst-forming reaction mixture with a carboxylic acid to rhodium mole ratio of at least about 2, and (II) maintaining the catalyst-forming reaction mixture at a temperature and pressure sufficient to complex (a), (b) and (c).

This invention further relates to a catalyst intermediate comprising a solid complex of the formula:

   Formula I wherein R is a triorganophosphine ligand, preferably a triaryl phosphine, L is a carboxylate ligand having a phenyl group substituted at the para position with an electron-withdrawing group that is substantially non-reactive under hydrocarbonylation conditions and that is free of further substitution, x has a value from about 0.8 to about 1.2, y has a value of about 2.0 to about 2.8, and z has a value of about 1.7 to about 2.2, the mole ratio of y to x is from about 1.8 to about 2.2, and the mole ratio of z to x is from about 2.0 to about 2.6. Preferably, L is derived from a benzoic acid substituted at the para position with a substantially non-reactive electron-withdrawing group and free of further substitution.

Formula I is representative of a dimeric complex having about two rhodium atoms per molecule, wherein said rhodium atoms are held together by about four bridging carboxylate ligands and wherein each of said rhodium atoms is bonded to about two phosphine ligands.

BRIEF DESCRIPTION OF THE DRAWINGS

FIGS. 1, and 3 are further described in Examples 34 to 39.

DETAILED DESCRIPTION OF THE INVENTION

Figure 1:
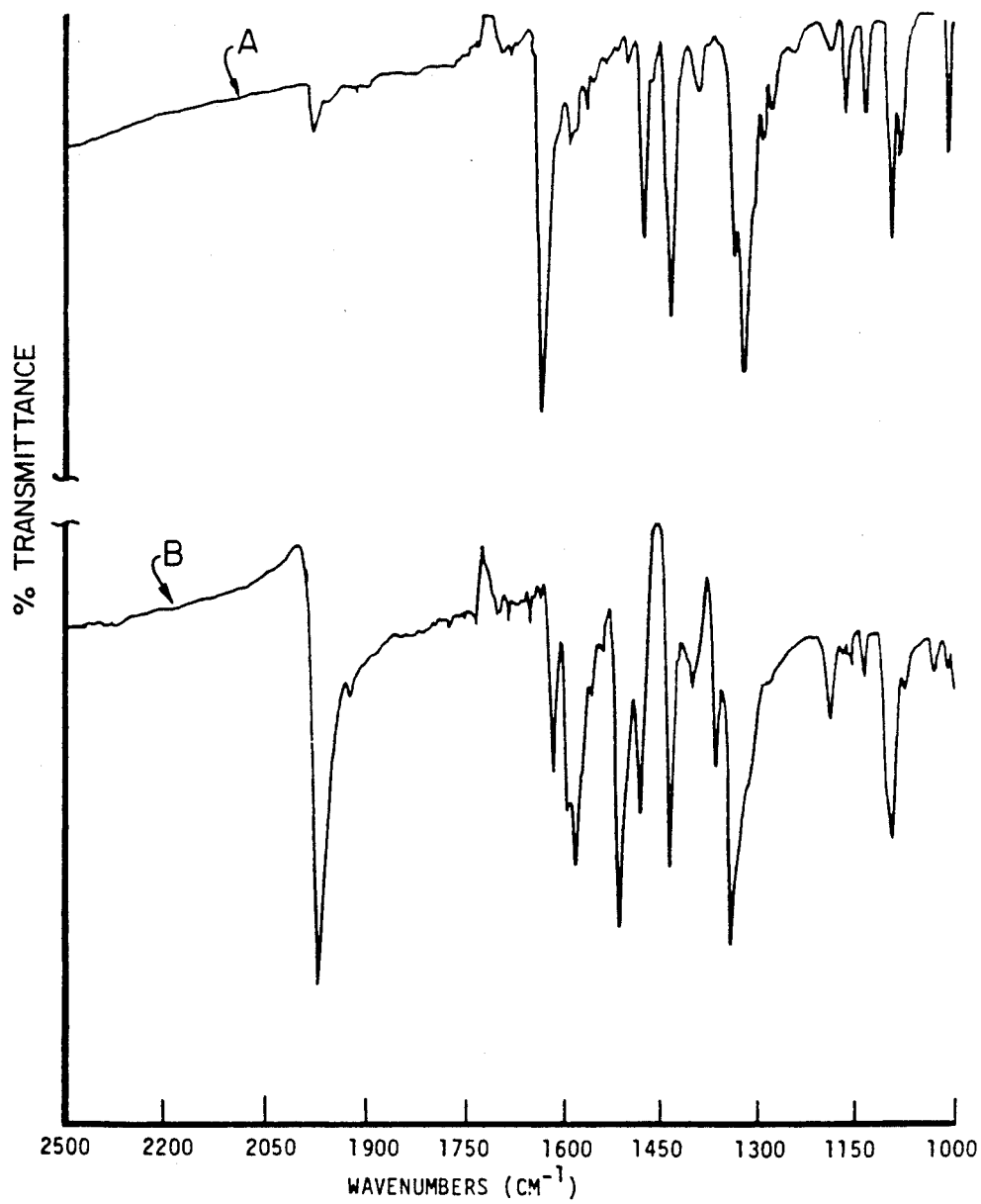
FIG. 1 provides infra red spectra of a square planar rhodium compound as described in British Pat. No. 1,181,806 (Spectrum B) and an isolatable complex intermediate of this invention (Spectrum A).
Figure 2:
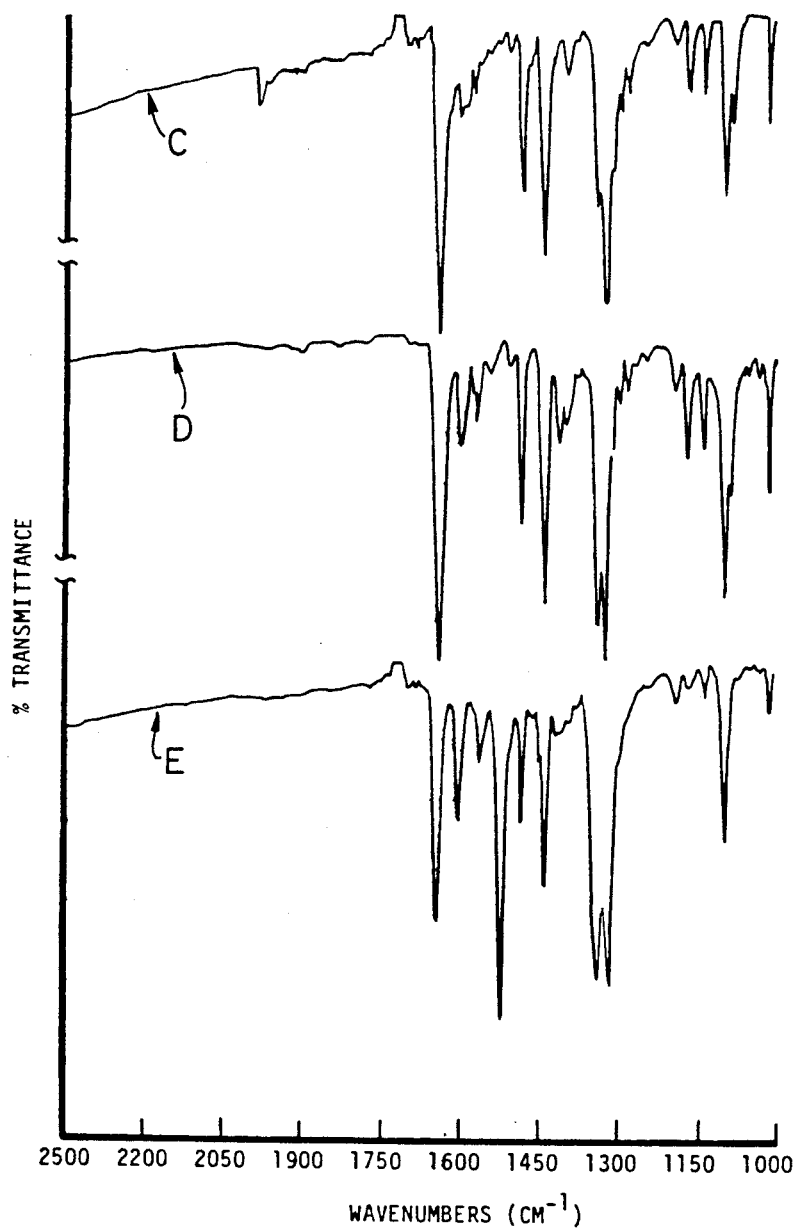
FIGS. 2 and 3 provide infra red spectra of several of the isolatable complex intermediates of the subject invention.
Figure 3:
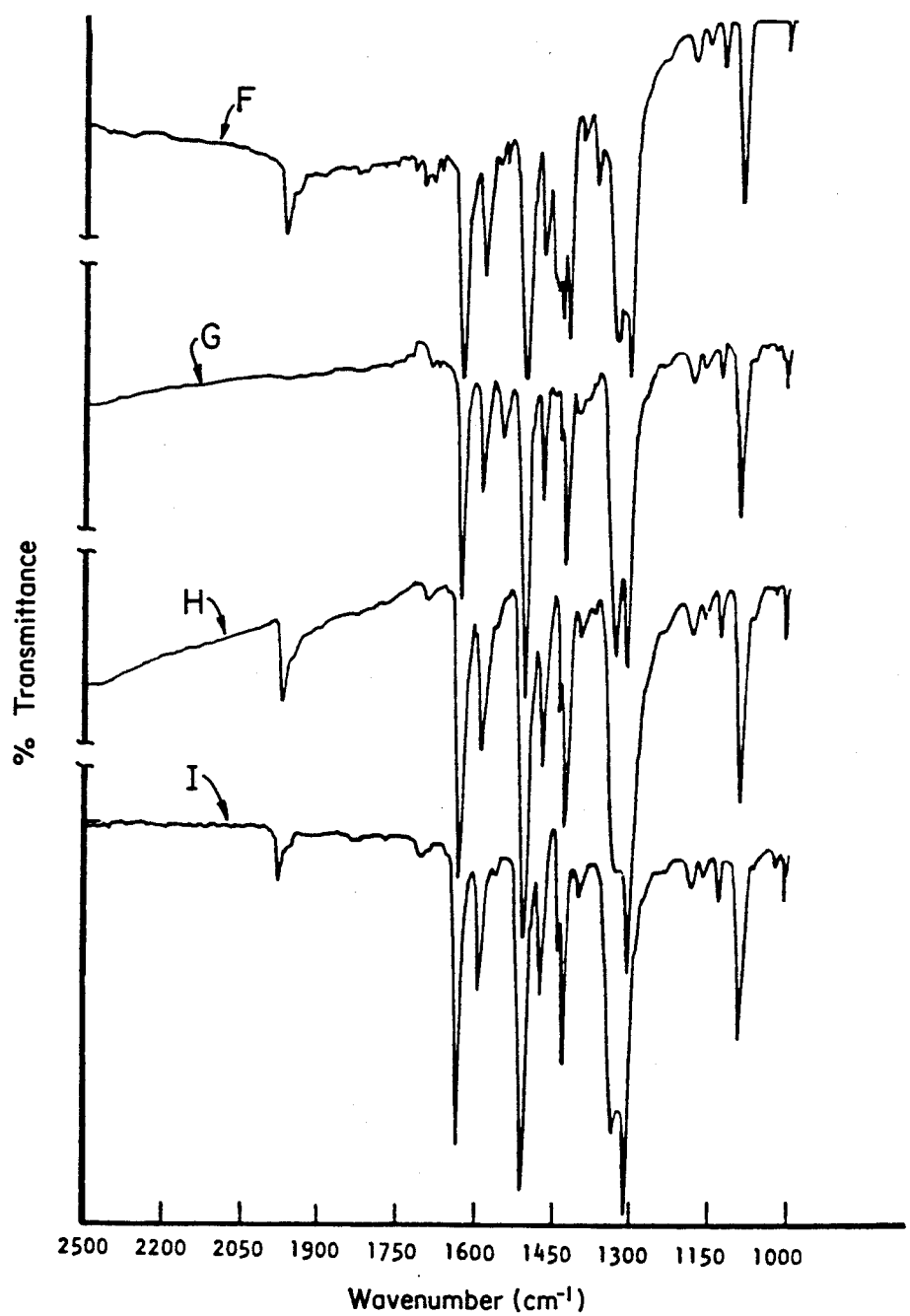

In accordance with the present invention there is provided a process for producing an aldehyde or a mixture of a ketone and an aldehyde wherein a reaction mixture comprising:

(a) a complex catalyst consisting essentially of rhodium in complex combination with
 (i) a triorganophosphine and
 (ii) a carboxylic acid having a para-substituted phenyl group and free of further substitution;
(b) an alpha olefin having 2 to 5 carbon atoms inclusive;
(c) carbon monoxide; and
(d) hydrogen is heated under pressure to form the desired aldehyde or mixture of ketone and aldehyde.

Triorganophosphines suitable for use in the process of this invention include substituted and unsubstituted triaryl phosphines such as, for example, triphenyl phosphine, trinaphthyl phosphine, tris(methylphenyl) phosphine, tris(chlorophenyl) phosphine, tris(fluorophenyl) phosphine, tris(methoxyphenyl) phosphine, tris(biphenyl) phosphine, (N,N-dimethylamino)phenyl diphenyl phosphine, and the like, with triphenyl phosphines and para-substituted triphenyl phosphines representing a preferred class of triaryl phosphines; substituted and unsubstituted alkyl diaryl phosphines such as, for example, methyldiphenyl phosphine, ethyldiphenyl phosphine, propyldiphenyl phosphine, butyldiphenyl phosphine, butyl-bis(chlorophenyl) phosphine, ethyl-bis(methoxyphenyl) phosphine, ethyl-phenyl-biphenyl phosphine, methyl-phenyl-(N,N-dimethylamino phenyl) phosphine, and the like, with diphenyl phosphines having para-substituted phenyl groups representing a preferred class of substituted alkyldiaryl phosphines; substituted and unsubstituted dialkylaryl phosphines such as, for example, dimethylphenyl phosphine, diethylphenyl phosphine, dipropylphenyl phosphine, dibutylphenyl phosphine, dibutyl(chlorophenyl) phosphine, dibutyl(methylphenyl) phosphine, dicyclohexylphenyl phosphine, and the like, with dialkylphenyl phosphines having para substituted phenyl groups representing a preferred class of substituted dialkylaryl phosphines. For purposes of this invention triaryl phosphines represent the preferred class of triorganophosphines.

As a general rule, the phosphines employed in the process of this invention should be free of substituents which tend to deactivate or poison a catalyst (e.g., sulfone, cyano, and mercapto groups). Whereas, tris(p-chlorophenyl) phosphine is suitable for use herein, phosphines which contain loosely bonded iodo groups should be avoided, since free halides are known catalyst deactivators. Further, in order to provide an acceptable rate of reaction, the phosphines should be free of sterically hindered groups. Phosphines characterized by the presence of "bulky groups" such as, for example, tris(o-tertiarybutyl)phosphine are undesirable when relatively rapid reactions are desired.

The mole ratio of triorganophosphine to rhodium present in a reaction mixture has a significant effect on process selectivity. When a reaction mixture has a mole ratio of phosphine to rhodium in excess of about 4, the ability of the catalyst present therein to catalyze ketone production, can be significantly impaired. In general, ketone selectivity of a process is enhanced when the reaction mixture contains up to about 3, preferably from about 1 to about 2 moles of triorganophosphine per mole of rhodium.

At elevated temperatures, typically temperatures in excess of about 80° C., it is possible for certain of the previously described para-substituted carboxylic acids (e.g., p-nitrobenzoic acid) to oxidize phosphines to phosphine oxides. Thus, solutions of complex catalysts wherein the mole ratio of triorganophosphine to rhodium initially exceeds about 4 may oftentimes be rendered suitable for use in ketone production by (a) providing the solution with a para-substituted carboxylic acid having oxidizing capability, in an amount sufficient to convert excess phosphine to phosphine oxide and (b) heating the resultant solution to a temperature sufficient to effect phosphine oxidation. Phosphine oxide does not have the deleterious effect of excess phosphine on the process of this invention.

Carboxylic acids suitable for use in the process of this invention are characterized by the presence of a phenyl group para-substituted with a non-reactive electron-withdrawing group and free of further substitution. Preferably, the non-reactive electron-withdrawing group is at least as electron-withdrawing as chlorine. For purposes of this invention the electron-withdrawing ability of a group is determined by comparing the Hammett sigma substituent constant for the ionization of benzoic acid substituted in the para position with said group with the Hammett sigma substituent constant for the ionization of benzoic acid in water at a constant temperature.

As used herein, a "substantially non-reactive electron-withdrawing group" is an electron-withdrawing group which does not react to any substantial degree with the gaseous components of a reaction mixture (i.e., alpha-olefin, carbon monoxide and hydrogen) under the reaction conditions employed. Accordingly, carboxylic acids such as, for example, p-cyanobenzoic acid are unsuitable for use in the practice of this invention since reduction of the cyano group by gaseous hydrogen produces an unstable catalyst.

Included among the acids suitable for use in the process of this invention are halo-substituted benzoic acids such as p-chlorobenzoic acid and p-fluorobenzoic acid; p-nitrobenzoic acid; alkyl-substituted benzoic acids wherein said alkyl group has 1 to 6 carbon atoms and at least one group at least as electron-withdrawing as chlorine, such as, for example, p-(trisfluoromethyl)benzoic acid. For purposes of this invention, p-chlorobenzoic acid, p-fluorobenzoic acid and p-nitrobenzoic acid, are found to provide catalysts having a relatively high degree of selectivity toward ketone production. It has been found that substitution at the para position of an acid's phenyl group is a critical factor in achieving complex stabilization. Complexes which contain ortho-substituted acids, such as o-chlorobenzoic acid, or poly-substituted acids, such as 3,4-dichlorobenzoic acid, tend to produce catalysts that have significantly less life than catalysts containing the para-substituted acids herein described. The selectivity of a reaction toward ketone production is generally enhanced when the mole ratio of the para-substituted carboxylic acid to rhodium present in a reaction mixture is at least about 2, preferably is at least about 7, and most preferably is at least about 14.

Alpha-olefins which can be employed in the process of this invention are organic compounds having 2 to 5 carbon atoms inclusive, preferably 2 to 4 carbon atoms inclusive, including alpha-olefins in which the terminal ethylene group is a vinylidene group (i.e., $CH_2=C-$)

or a vinyl group (i.e., $CH_2=CH-$). The alpha-olefins may be straight chain or branched chain compounds and may contain substituents which do not interfere with the hydroformylation and/or hydroacylation reactions herein involved.

Illustrative alpha-olefins useful in the process of this invention include ethylene, propylene, 1-butene, 1-pentene, as well as alpha-olefins substituted with a functional group, such as for example allyl alcohol, allyl acetate, 3-butenoic acid, and the like. For purposes of this invention, preferred alpha-olefins are alpha-olefins selected from the group consisting of ethylene, propylene and 1-butene, with ethylene and propylene being the alpha-olefins of choice when a ketone product is desired. Although the catalysts of this invention may be employed with any of the above-described olefinic reactants to produce various aldehyde products, when ketone production is desired, the preferred olefinic reactants are limited to linear alpha-alkenes.

The reaction mixtures of this invention may contain an organic compound which is a solvent for the complex catalyst as previously described and which does not interfere to any substantial degree with the particular reaction involved under the hydrocarbonylation conditions employed. Solvents which may be employed in the hydroformylation reactions of this invention include the saturated hydrocarbons such as, naptha, kerosene, mineral oil, cyclohexane, and the like, as well as the aromatic hydrocarbons, ethers, ketones, and aldehydes as illustrated by benzene, xylene, toluene, diethyl ether, acetophenone, cyclohexanone, propionaldehyde, and the like. One preferred class of solvents for hydroformylation reactions includes the aldehydes to be produced in the given reaction. Another preferred class of hydroformylation solvents includes the high boiling aldehyde condensation products illustrated by 2,2,4-trimethyl pentanediol 1,3-monoisobutyrate. Suitable solvents for hydroacylation reactions include ketones, such as, for example, pentanones, heptanones, octanones and the like; as well as organic ethers such as the dimethyl ethers of diethylene glycol, triethylene glycol, tetraethylene glycol, and the like. 3-pentanone, 4-heptanone and the dimethyl ether of tetraethylene glycol are preferred solvents for hydroacylation reactions.

The quantity of organic solvent which may be employed in the process of this invention is subject to variation, and need only be that amount sufficient to solubilize the particular rhodium complex catalyst therein. In general the amount of solvent employed in a reaction medium may be as little as about 5 weight percent of the reaction mixture.

In general, the processes of this invention are conducted at a reaction temperature of from about 50° C. to about 200° C., preferably from about 90° C. to about 150° C., and most preferably from about 100° C. to about 110° C., and a total gas pressure of alpha-olefin, carbon monoxide and hydrogen of less than about 525 psi, preferably from about 100 psi to about 300 psi and most preferably from about 100 psi to about 175 psi. While it may be possible to conduct the processes of this invention at temperatures and pressures outside of the limits described above, economic factors would not favor their use.

Typically, the process of this invention is carried out under conditions wherein the partial pressure attributable to carbon monoxide is from about 5% to about 75% of the total pressure of the alpha-olefin, carbon monoxide and hydrogen. The partial pressure attributable to hydrogen and alpha-olefin is subject to variation depending upon the particular product desired. For example, when the partial pressure of carbon monoxide comprises from about 5 to about 20 percent of the total pressure of carbon monoxide, hydrogen and alpha-olefin, and a product rich in ketone is desired, the ratio of the partial pressure of alpha-olefin to the partial pressure of hydrogen should range from about 5/1 to about 1/5. When the partial pressure of carbon monoxide comprises from about 21 to about 50 percent of the total pressure of carbon monoxide, hydrogen and alpha-olefin, and a product rich in ketone is desired, the ratio of the partial pressure of alpha-olefin to the partial pressure of hydrogen should range from about 5/1 to about 2/1. Within the above described carbon monoxide partial pressure ranges and outside of the lower limits of the recited alpha-olefin to hydrogen partial pressure ratios, the selectivity of the process of this invention toward aldehyde production is generally enhanced. In general, aldehyde selectivity is also enhanced at carbon monoxide partial pressures in excess of about 50 percent of the total pressure of carbon monoxide, alpha-olefin and hydrogen, thus, reaction conditions wherein the partial pressure of carbon monoxide is from about 5 to about 50% of the total pressure of alpha-olefin, carbon monoxide and hydrogen are recommended when a ketone-rich product is desired.

The reactions of this invention are found to proceed in the presence of as little as $1\times10^{-5}$ mol of rhodium, per mol of alpha-olefin. However, such catalyst concentrations, though operable, generally do not proceed at commercially attractive rates. For purposes of this invention, catalyst concentrations of from about $1.5\times10^{-4}$ mol to about $1.0\times10^{-2}$ mol of rhodium per mol of alpha-olefin are desirable, with catalyst concentrations of from about $1.5\times10^{-4}$ mol to about $5.0\times10^{-3}$ mol of rhodium per mole of alpha-olefin being preferred. That quantity of catalyst which is effective in catalyzing the processes of this invention is herein termed a "catalytically effective amount" of catalyst.

The processes of this invention may be carried out batch wise, or preferably, in a continuous manner according to procedures which are generally known in the art.

The catalysts used in the process of this invention consist essentially of rhodium in complex combination with a triorganophosphine and a carboxylic acid having a phenyl group substituted at the para-position with an electron-withdrawing group. As used herein, the term "complex" means a coordination compound formed by the union of one or more electronically- rich molecules or atoms capable of independent existence with one or more electronically poor molecules or atoms, each of which is also capable of independent existence. The triorganophosphines function as ligands by forming a coordinate bond with rhodium through the unshared electron pair of the phosphorous atom thereof. Similarly, the para-substituted carboxylic acids form bonds with rhodium through the unshared electron pairs of each of the two oxygen atoms present in the carboxylate groups thereof, and thus may function as "bridging" ligands between separate rhodium atoms. It is not intended that the present invention be limited by any single explanation as to the exact structure of the complex catalyst. As used herein, the term "active catalyst" means that particular form of catalyst complex which exists at the point of reaction between the gaseous components of a reaction mixture. The active catalyst present during a reaction may, in fact, be a rhodium cluster compound formed by the various reaction mixture components under reaction conditions.

The active catalyst may also contain one or more additional ligands. For example, the active catalyst is known to contain carbon monoxide as a ligand, the carbon monoxide component of the reaction mixture being expected to compete with phosphine and carboxylate ligands for complexing sites with rhodium. The ability of carbon monoxide to compete for sites on the active catalyst will be determined in part on factors which include the partial pressure of carbon monoxide in the feed gas composition as well as the concentration of para-substituted carboxylic acid and triorganophosphine present in the reaction mixture. Likewise, the active catalyst may also contain hydrogen as a ligand.

Various rhodium sources may be used to form the complex catalysts used in the process of this invention. Rhodium sources suitable for use herein include rhodium oxides, such as, for example, rhodium sesquioxide ($Rh_2O_3$), rhodium carbonyl compounds, such as, for example $Rh_4(CO)_{12}$ and $Rh_6(CO)_{16}$, rhodium dicarbonyl acetylacetonate (hereinafter $Rh(CO)_2(AcAc)$), and both neutral and cationic species of rhodium carbonyl compounds in complex combination with triorganophosphines such as, for example, rhodium fluorocarbonyl-bis(triphenyl phosphine) (hereinafter $RhF(CO)(TPP)_2$), rhodium hydridocarbonyl-tris(triphenyl phosphine) (hereinafter $RhH(CO)(TPP)_3$), rhodium octadecylcarbonyl-bis(triphenyl phosphine) tetraphenyl borate hereinafter $[Rh(COD)(TPP)_2]^+BPh_4^-$, and the like. The rhodium source employed should be free of groups which tend to deactivate or poison the complex (e.g. halo or sulfur groups bonded directly to the rhodium atom).

Chlorine atoms directly bonded to rhodium are frequently found to adversely effect the performance of the catalysts used in the process of of this invention. Accordingly, rhodium sources such as for example, bis-rhodium chlorodicarbonyl (($Rh(Cl)(CO)_2)_2$) and rhodium chlorocarbonyl bis(triphenyl phosphine) ($Rh(Cl)(CO)(C_6H_5)_3P)_2$) are not recommended for use herein. For purposes of this invention, preferred rhodium sources are rhodium carbonyl compounds, particularly those compounds selected from the group consisting of $Rh(CO)_2(AcAc)$, $RhF(CO)(TPP)_2$, $RhH(CO)(TPP)_3$ and $[Rh(COD)(TPP)_2]^+BPh_4^-$.

In addition to serving as a rhodium source, rhodium carbonyl compounds which contain triorganophosphine groups (e.g. $RhF(CO)(TPP)_2$) may also act as the triorganophos-phine source in the preparation of the complex catalysts of this invention.

The complex catalysts used in the process of this invention are typically prepared by heating a catalyst-forming reaction mixture comprising (a) a para-substituted carboxylic acid as previously described, (b) a rhodium source (c) a triorganophosphine source and (d) a non-reactive organic compound which is a solvent for (a), (b) and (c) at a temperature sufficient to complex the rhodium, para-substituted benzoic acid and triorganophosphine. Preferably, the catalysts of this invention are prepared by heating the catalyst forming reaction mixture in an inert atmosphere (desirably a nitrogen atmosphere). The constraints previously discussed in the context of the hydrocarbonylation reaction mixture with respect to carboxylic acid to rhodium mole ratios are applicable to the formation of catalyst forming reaction mixtures. Preferably, the mole ratio of triorganophosphine to rhodium present in the catalyst-forming reaction mixture is not in excess of about 4.

Non-reactive compounds suitable for use as solvents in the formation of the complex catalysts of this invention are those compounds previously discussed in the context of solvents suitable for use in hydroacylation processes. The temperatures at which the catalysts of this invention form is subject to variation, depending in part upon factors which include selection of catalyst forming reaction mixture components, reaction pressures and the like. In general, catalyst-forming temperatures range from about 20° C. to temperatures in excess of about 140° C. In some instances, catalyst formation is preceded by the formation of an isolatable solid intermediate, represented by Formula I above, as a yellow precipitate which, upon further heating, is returned to solution. The complex catalysts of this invention may be preformed or produced in situ by maintaining the above described complex forming conditions during hydrocarboxylation.

EXAMPLES

The following Examples are illustrative of the present invention. It is not intended, however, that the scope of the invention be limited by the Examples. Unless otherwise indicated, all of the parts and percentages referred to in the following Examples are by weight.

EXAMPLES 1 TO 9

This series of Examples serves to illustrate the effect of various acids on catalyst stability and reaction selectivity under hydroacylation conditions.

The reactor used in these Examples was a 150 ml mini-reactor suitable for use at pressures up to 500 psi. The reactor was equipped with a magnetic stirrer, overhead gas inlet, temperature controller, liquid outlet tube and gas manifold.

Rhodium dicarbonylacetylacetonate ($Rh(CO)_2AcAc$), triphenyl phosphine (TPP), and a selected acid, as noted in Table I below, were dissolved under a nitrogen atmosphere, in 30 grams of dipropylketone at a temperature of 20° C.±5° C. to provide catalyst solutions containing about 150 ppm of rhodium (calculated as the free metal) and having a TPP to rhodium mole ratio of 1:1 and an acid to rhodium mole ratio of 13.8:1.

Thereafter 25 ml of catalyst solution was introduced to the reactor which had been evacuated to a pressure of 200 mm Hg. The reactor was then flushed, with three separate sparges of nitrogen of 30 psig, vented to a pressure of about 0.5 psig, and heated to a temperature of 100° C. A premixed feed gas consisting of ethylene, carbon monoxide and hydrogen at a partial pressure ratio of ethylene:hydrogen:carbon monoxide of 124 psi:29 psi:12 psi was charged to the reactor to provide an operating pressure of 165 psi. The reactor was maintained at a temperature of 100° C. and as the reaction proceeded, the time required to obtain pressure drop increments of 5 psi was recorded. Following each pressure drop of 5 psi the reactor was repressurized to the original operating pressure of 165 psi by the addition of a mixture of carbon monoxide and hydrogen having a carbon monoxide to hydrogen mole ratio of 1/1. During the course of reaction the precipitation of some of the rhodium from the catalyst solution as a black solid was noted. The reaction was discontinued when the time period to obtain a pressure drop of 5 psi became relatively constant, as determined by at least about five consecutive measurements. The average value of these relatively constant consecutive measurements is herein termed the "constant pressure drop period." Reactions were also discontinued when it became apparent that the pressure drop periods would not level off, in which case the "constant pressure drop period" was taken to be the average value of those consecutive measurements deemed to most closely approximate a constant period for a 5 psi drop in pressure. Upon discontinuance of the reaction, the resultant liquid product was discharged into a vessel which was contained in a dry ice acetone bath and maintained under a nitrogen atmosphere. Thereafter, the resultant product was weighed and subjected to atomic adsorption spectroscopy and gas chromatographic analysis to determine the amount of rhodium, aldehyde and ketone present therein.

The stability of the various catalyst solutions was determined by comparing the amount of rhodium which remained in the liquid product at the expiration of the test with the amount of rhodium which was initially present in the catalyst solution. The percentage of precipitated rhodium is reported in Table I as the "% Rh Loss." As used herein $$\% \; Rh \; Loss = 100 - (C_I - C_E/C_I)100 \quad \text{Formula II}$$

wherein $C_I$ is the amount of rhodium initially present in a catalyst solution, and $C_E$ is the amount of rhodium remaining in the liquid product at the expiration of the reaction.

The production rates of diethylketone and propionaldehyde produced by the above described reactions are reported in Table I as "$R_K$" and "$R_A$" respectively. For this series of Examples aldehyde and ketone production rates and ($R_A$ and $R_K$) are calculated by means of the following formulas:

$$R_A = \frac{n_a P t}{R V t_p} \left( \frac{V_{int}}{T_1} + \frac{V_{ext}}{T_2} \right) \quad \text{Formula III}$$

wherein

P is the pressure drop increment of 5 psi, t is a conversion factor of 3600 seconds/hour, $t_p$ is the constant pressure drop period as previously defined, in seconds, $n_a$ is the weight fraction of aldehyde produced divided by the sum of (a) the product of 4 times the weight fraction of ketone produced and (b) the product of 3 times the weight fraction of aldehyde produced, wherein all weight fractions are based on the total weight, in grams, of aldehyde and ketone produced.

R is a gas constant of 1.206 liter psi/°K.,

V is the volume of the catalyst solution in liters, $V_{int}$ is the volume of the reactor minus the volume of the catalyst solution, in liters, $V_{ext}$ is sum of the volumes, in liters, of the lines to the reactor from the premixed ethylene/carbon monoxide/hydrogen and carbon monoxide/hydrogen feed sources, $T_1$ is the temperature of the reactor contents in °K., and $T_2$ is the ambient temperature in °K.; and $$R_K = \frac{n_k P t}{R V t_p} \left( \frac{V_{int}}{T_1} + \frac{V_{ext}}{T_2} \right) \quad \text{Formula IV}$$

wherein

P, t, $t_p$, R, V, $V_{int}$, $V_{ext}$, $T_1$ and $T_2$ are as described above and $n_k$ is the weight fraction of ketone produced divided by the sum of (a) the product of 4 times the weight fraction of ketone produced and (b) the product of 3 times the weight fraction of aldehyde produced wherein all weight fractions are based on the total weight, in grams, of aldehyde and ketone produced.

Formula III and IV take into account the fact that 4 moles of gas are required to produce 1 mole of a ketone product, whereas, 3 moles of gas are required to produce 1 mole of an aldehyde product. $R_A$ and $R_K$ are expressed in units of qram-moles per liter hours.

The data presented in Table I shows that a catalyst solution containing p-nitrobenzoic acid, a solution illustrative of the practice of this invention, was considerably more stable and more selective with respect to ketone production than comparative catalyst solutions containing other acids (including unsubstituted benzoic acid), some of which did not catalyze the reaction at all.

TABLE I

| Example [1] | Acid | R K | R A | % Rhodium Loss[2] |
|---|---|---|---|---|
| 1 | Trifluormethane sulfonic | No Reaction | | |
| 2 | Phenyl phosphonic acid | No Reaction | | |
| 3 | Acetic | 0.7 | 3.0 | 21.8 (15.5) |
| 4 | Trifluoroacetic | No Reaction | | |
| 5 | Octanoic | 1.6 | 4.8 | 8.3 (6.4) |
| 6 | Perfluorooctanoic | 1.2 | 0.2 | 14.8 (9.9) |
| 7 | Benzoic | 1.2 | 10.7 | 9.6 (7.2) |
| 8 | Pentafluorobenzoic | 1.0 | 0.7 | 21.6 (17.1) |
| 9 | p-Nitrobenzoic | 2.1 | 4.8 | 3.0 (2.1) |

[1] Examples 1 through 8 are provided for comparative purposes.
[2] Numbers in parenthesis represent rhodium loss data for a repeat run of a given Example.

EXAMPLES 10 to 19

The following Examples serve to illustrate the differences in catalyst stability and process selectivity obtained utilizing catalyst solutions containing various benzoic acids under hydroacylation conditions. The data further demonstrates the criticality of substituent selection and position.

The reactor used in Examples 11 to 20 was a 300 ml autoclave equipped with a magnetic stirrer, overhead gas inlet, temperature controller, liquid outlet tube and gas manifold.

In this series of Examples, rhodium dicarbonylacetylacetonate (Rh(CO)$_2$AcAc), triphenyl phosphine (TPP) and a selected acid as noted in Table II below, were dissolved under a nitrogen atmosphere in dipropyl ketone to provide catalyst solutions containing about 150 ppm of rhodium (calculated as the free metal) and having a mole ratio of TPP to rhodium of 1:1, and an acid to rhodium mole ratio of 13.8:1. The temperature at which catalyst solution components were found to go into solution is provided in Table II.

For each reaction, 25 ml. of catalyst solution was introduced to the reactor and heated to a temperature of 100° C. Thereafter, a premixed feed gas consisting of ethylene, carbon monoxide and hydrogen at a partial pressure ratio as indicated in Table II was charged to the reactor to provide an operating pressure of 515 psi.

The reactor was then maintained at an operating temperature of 100° C. for a period of ten minutes during which time a drop in the overall reaction pressure was observed. At the expiration of the 10 minute reaction period the reactor was cooled to a temperature of 25° C. over a period of about 30 minutes and the liquid product discharged into a vessel which was contained in a dry ice-acetone bath and maintained under a nitrogen atmosphere. During the course of the reaction, the precipitation of some of the rhodium from the catalyst solution as a black solid was noted. Thereafter the resultant ligand product was weighed and subjected to gas chromatographic analysis and atomic adsorption spectroscopy to determine the relative quantities of diethyl ketone and propionaldehyde produced. Product production rates ($R_K$ and $R_A$) were determined by; (1) dividing the number of moles of ketone or aldehyde produced, by the product of (a) the molecular weight of same and (b) the quantity of catalyst solution charged to the reactor, in liters, and (2) multiplying the resultant value by six to convert same to a one hour basis. Production rates are expressed in units of g-moles per liter-hours. Production rates and rhodium loss data calculated as described in Examples 1 to 9 are provided in Table II.

The data presented in Table II shows that catalyst solutions containing benzoic acids substituted at the para position with a non-reactive electron withdrawing group tend to be more stable than comparative catalyst solutions containing benzoic acids substituted at the para position with an electron donating group such as a methoxy or dimethylamino group. The data also shows that substitution of the benzoic acid component of a catalyst solution at other than the para position has a deleterious effect on catalyst stability (compare Examples 16 and 17 which illustrate this invention with comparative Examples 18 and 19). As shown by comparative Example 12, benzoic acids substituted with a reactive group such as a cyano group are generally unstable.

TABLE II

| Example[1] | Acid | Solution Formation Temperature (°C.) | Gas Ratio[2] | $R_K^o$ | $R_A^o$ | % Rh Loss |
|---|---|---|---|---|---|---|
| 10 | None | 20 | a | 3.7 | 3.7 | 42 |
| 11 | Benzoic | 20 | a | 8.3 | 3.1 | 62 |
| 12 | p-cyanobenzoic | 90 | b | 5.2 | 1.0 | 22 |
| 13 | p-dimethylamino benzoic | 75 | b | 2.7 | 7.3 | 0 |
| 14 | p-methoxy benzoic | 60 | b | 3.0 | 2.4 | 50 |
| 15 | m-methyl benzoic | 20 | b | 4.0 | 1.0 | 19 |
| 16 | m-trifluoromethyl benzoic | 20 | b | 6.8 | 1.7 | 26 |
| 17 | o-chlorobenzoic | 20 | b | No reaction | | |
| 18 | p-nitrobenzoic | 95 | b | 6.0 | 0.8 | 0 |

[1]Examples 10 through 17 are provided for comparative purposes.
[2]A gas ratio of $C_2H_4:CO:H_2$ of 309 psi:154 psi:52 psi is designated by the letter "a". A gas ratio of $C_2H_4:CO:H_2$ of 232 psi:51 psig:232 psi is designated by the letter "b".

EXAMPLES 19 to 33

The data presented by these Examples demonstrates how the mole ratio of triorganophosphine to rhodium present in a catalyst solution effects process selectivity.

The minireactor previously described in Example 1 was employed in this series of reactions.

Catalyst solutions containing the rhodium, para substituted benzoic acid and triphenyl phosphine (TPP) components described in Table III were prepared by dissolving the various solution components in dipropyl ketone under a nitrogen atmosphere. The solutions were formulated to contain 300 ppm of rhodium (calculated as the free metal). When present, the para-substituted benzoic acid was added to the solution in an amount sufficient to provide an acid to rhodium mole ratio of 30:1. The temperature at which catalyst solution components were found to go into solution is provided in Table III. The various catalyst solutions were thereafter reacted according to the procedure described in Examples 1 to 9. Diethylketone and propionaldehyde production rates for this series of reactions, calculated as described in Example 1 to 9, are provided in Table III.

Examples 20, 23, 25, 28 and 30 show that the p-nitro and p-chlorobenzoic acid-containing catalyst solutions of this invention provide greater selectivity toward ketone production than catalyst solutions containing an identical rhodium source and having the same mole ratio of TPP to rhodium but lacking an acid component (see comparative Examples 19, 22 and 27).

The data further shows that catalyst solutions containing p-nitrobenzoic acid were able to catalyze ketone production at higher triphenyl phosphine to rhodium mole ratios than catalyst solution containing p-chlorobenzoic acid. (Compare Examples 23 and 26, and Examples 28, 30 and 31). Comparative Examples 29 and 33 show that at a total phosphine to rhodium mole ratio of 5, neither the p-nitrobenzoic acid nor p-chlorobenzoic acid-containing solutions were able to catalyze ketone production.

TABLE III

| Example | Rhodium Rh Source | Solution Formation Temperature (°C.) | Added TPP (moles of TPP per mole of Rh) | Total phosphine (moles of phosphine present in the catalyst solution per mole of Rh) | Added Acid | $R_K$ | $R_A$ |
|---|---|---|---|---|---|---|---|
| 19 | Rh(CO)$_2$AcAc | 23 | 1 | 1 | none | 1.1 | 10.5 |
| 20 | Rh(CO)$_2$AcAc | 50 | 1 | 1 | p-chlorobenzoic | 8.9 | 7.9 |
| 21 | Rh(CO)$_2$AcAc | 45 | 4 | 4 | p-chlorobenzoic | 0 | 1.9 |

TABLE III-continued

| Example | Rhodium Rh Source | Solution Formation Temperature (°C.) | Added TPP (moles of TPP per mole of Rh) | Total phosphine (moles of phosphine present in the catalyst solution per mole of Rh) | Added Acid | $R_K$ | $R_A$ |
|---|---|---|---|---|---|---|---|
| 22 | RhF(CO)(TPP)$_2$ | 24 | 0 | 2 | none | 1.1 | 9.4 |
| 23 | RhF(CO)(TPP)$_2$ | 50 | 0 | 2 | p-chlorobenzoic | 3.5 | 6.2 |
| 24[1] | RhF(CO)(TPP)$_2$ | 20 | 2 | 4 | p-chlorobenzoic | 0 | 2.7 |
| 25[2] | RhF(CO)(TPP)$_2$ | 140 | 0 | 2 | p-nitrobenzoic | 1.7 | 1.2 |
| 26[2] | RhF(CO)(TPP)$_2$ | 140 | 2 | 4 | p-nitrobenzoic | 2.0 | 2.2 |
| 27 | [Rh(COD)(TPP)$_2$]$^{30}$ BPh$_4$$^-$ | 20 | 0 | 2 | none | 1.4 | 14.7 |
| 28[1] | [Rh(COD)(TPP)$_2$]$^+$BPh$_4$$^-$ | 60 | 0 | 2 | p-chlorobenzoic | 3.7 | 5.2 |
| 29[1] | [Rh(COD)(TPP)$_2$$^+$BPh$_4$$^-$ | 80 | 3 | 5 | p-chlorobenzoic | 0 | 2.1 |
| 30 | [Rh(COD)(TPP)$_2$]$^+$BP$_4$$^-$ | 30 | 0 | 2 | p-nitrobenzoic | 4.8 | 2.8 |
| 31[3] | [Rh(COD)(TPP)$_2$]$^+$BPh$_4$$^-$ | 100 | 2 | 4 | p-nitrobenzoic | 3.9 | 0.4 |
| 32[4] | HRh(CO)(TPP)$_3$ | 140 | 0 | 3 | p-nitrobenzoic | 3.1 | 1.6 |
| 33[4] | HRh(CO)(TPP)$_3$ | 140 | 2 | 5 | p-nitrobenzoic | No Reaction | |

[1] 25 ml of the dimethylether of tetraglyme was employed as the solvent rather than diethylketone.
[2] All solids were found ot dissolve at 45° C.; continued heating of the solution caused precipitation of some solids at about 60° C., upon further heating to 140° C., all solids were found to dissolve.
[3] A small quantity of solids remained undissolved.
[4] Some precipitation of solids was found to occur during heating to dissolve solution components; all precipitate formed was found to dissolve at 140° C.

Isolatable intermediates of this invention were prepared by means of the procedures described in Examples 34 through 39.

EXAMPLE 34

In the following order, 29.48 grams of dipropyl ketone, 0.06 grams of rhodium fluorocarbonyl bis(triphenyl phosphine), 0.05 grams of triphenylphosphine and 0.41 grams of p-chlorobenzoic acid were charged to a 4 ounce (120 ml) narrow mouth bottle sparged with nitrogen. The resultant mixture was heated to 42° C., producing a clear yellow catalyst solution. Upon cooling, a fluffy white solid was observed to precipitate out of solution. The solution was thereafter heated to 100° C. over a period of about 40 minutes during which period formation of a cloudy precipitate was noted, removed from the heat source, and allowed to stand overnight at about 20° C.±5° C. Thereafter, the precipitate was filtered free of the solution, extracted twice with 5 ml of boiling acetone and dried. An infra red spectrum was obtained for the product and is provided in the Figures which follow as Spectra A and C.

EXAMPLE 35

29.39 grams of dipropylketone, 0.12 grams of rhodium fluorocarbonyl bis(triphenyl phosphine), 0.09 grams of triphenyl phosphine, and 0.40 grams of p-nitrobenzoic acid were combined as described in Example 34 to produce a mixture which was thereafter heated to a temperature of about 100° C. to produce a catalyst solution. As the solution was heated to such temperature, formation of a precipitate was noted. The solution was thereafter removed from the heat source and allowed to stand overnight at a temperature of about 20° C.±5° C. The precipitate was then filtered free of the solution, washed with 5 ml of water, extracted twice with 10 ml of acetone and dried. An infra red spectrum was obtrained for the product and is provided in the Figures which follow as Spectrum I.

EXAMPLE 36

88.85 grams of dipropyl ketone, 0.28 grams of rhodium octadecylcarbonylbis(triphenyl phosphine) tertaphenyl borate, 0.14 grams of triphenyl phosphine and 1.23 grams of p-chlorobenzoic acid were combined as described in Example 34 to produce a reaction mixture which was thereafter heated to and maintained at a temperature of 50° C. for a one-hour period to produce a catalyst solution. Upon cooling to a temperature of 20° C.±5° C., precipitate was observed. The precipitate was filtered free of the solution, washed with acetone, extracted twice with 5 ml of boiling acetone, and dried. An infra red spectrum was obtained for the product and is provided in the Figures which follow as Spectrum D.

EXAMPLE 37

29.42 grams of dipropylketone, 0.09 grams of rhodium octadecylcarbonylbis(triphenyl phosphine) tetraphenyl borate, 0.05 grams of triphenyl phosphine and 0.44 grams of p-nitrobenzoic acid were combined as described in Example 34 to produce a reaction mixture which was thereafter heated to and maintained at a temperature of 50° C. for a period of about 5 minutes to produce a catalyst solution. Upon cooling to a temperature of about 20° C.±5° C. formation of a precipitate was observed. The precipitate was filtered free of solution, washed with aceton and extracted with 5 ml of boiling acetone. An infra-red spectrum was obtained for the product and is provided in the figures which follow as Spectra E and G.

EXAMPLE 38

42.50 grams of dipropyl ketone, 0.27 grams of rhodium hydridocarbonyltris(triphenyl phosphine) and 1.46 grams of p-nitrobenzoic acid were combined as described in Example 34 to produce a reaction mixture which gas then heated to a temperature of 95° C. to produce a catalyst solution. As the mixture was heated to such temperature, formation of a precipitate was noted. The solution was thereafter removed from the heat source and allowed to cool to a temperature of 20° C.±5° C. The precipitate was filtered free of solution, washed three times with 15 ml of acetone, extracted once with 15 ml of boiling acetone and dried. An infrared spectrum was obtained for the product and is provided in the Figures which follow as Specrum F.

EXAMPLE 39

29.45 grams of dipropyl ketone, 0.02 grams of rhodium dicarbonyl acetylacetonate, 0.09 grams of triphenylphosphine and 0.44 grams of p-nitrobenzoic acid were combined as described in Example 34 to produce a mixture which was thereafter heated to 140° C., to produce a catalyst solution. The solution was thereafter allowed to stand overnight at a temperature of about 20±5° C. during which time formation of a precipitate was noted. The precipitate was filtered from the solution, washed twice with 25 ml of acetone and dried. An infrared spectrum was obtained for the product and is provided in the Figures which follow as Spectrum H.

For comparative purposes an IR spectra of Trans-Rh $(O_2CC_6H_4p-NO_2)(CO)(TPP)_2$ a square, planar complex designated as spectrum "B" is provided in FIG. 1.

Apart from vibrations, due to the nitro group being absent from intermediates prepared from p-chlorobenzoic acid, the spectra of the isolatable intermediates of Examples 34 to 39 are markedly similar to one another, and markedly different from the spectrum obtained for trans-Rh$(O_2CC_6H_4p-NO_2)(CO)(TPP)_2$, most notably, the characteristic peak at 1970 cm$^{-1}$ present in Spectrum B is absent from the spectra obtained for the complex intermediates of Examples 34 to 39.

What is claimed is:

1. A hydrocarbonylation process for producing a mixture of a ketone and an aldehyde which comprises:
   (I) forming a reaction mixture comprising:
      (a) a catalytic amount of a complex catalyst consisting essentially of rhodium in complex combination with
         (i) a triorganophosphine, and
         (ii) a carboxylic acid selected from the group consisting of p-chlorobenzoic acid, p-fluorobenzoic acid and p-nitrobenzoic acid,
      (b) an alpha-olefin having 2 to 5 carbon atoms inclusive,
      (c) carbon monoxide, and
      (d) hydrogen
      with the proviso that the reaction mixture has a mole ratio of said carboxylic acid to rhodium of at least about 2; and a mole ratio of said triorganophosphine to rhodium not in excess of about 4; and
   (II) maintaining the reaction mixture at a temperature and pressure at which said (b), (c) and (d) react to form a mixture of a ketone and an aldehyde.

2. A process as defined in claim 1 wherein the triorganophosphine is a member selected from the group consisting of substituted and unsubstituted triaryl phosphines, substituted and unsubstituted alkyl diaryl phosphines, and substituted and unsubstituted dialkyl phenyl phosphines.

3. A process as defined in claim 1 wherein the reaction mixture further comprises a organic compound which is a solvent for the complex catalyst and is essentially non-reactive in the process.

4. A process as defined in claim 1 wherein the reaction mixture is maintained at a temperature of from about 50° C. to about 200° C. and a total gas pressure of alpha-olefin, carbon monoxide and hydrogen of less than about 525 psi.

5. A process as defined in claim 4 wherein the alpha-olefin is ethylene.

6. A process as defined in claim 1 wherein the reaction mixture has a partial pressure of carbon monoxide of from about 5 percent to about 75 percent of the total gas pressure of alpha-olefin, carbon monoxide and hydrogen.

7. A process as defined in claim 1 wherein the mole ratio of carboxylic acid to rhodium is at least about 7.

8. A process as defined in claim 1 wherein the triorganophosphine is a substituted or unsubstituted triaryl phosphine.

9. A process as defined in claim 1 wherein the reaction mixture contains at least about $1\times10^{-5}$ mol of rhodium per mol of alpha-olefin.

10. A process as defined in claim 1 wherein the carboxylic acid is p-nitrobenzoic acid.

11. A process as defined in claim 1 wherein the triaryl phosphine is tri-phenylphosphine.

12. A process as defined in claim 1 wherein the reaction mixture has a partial pressure of carbon monoxide of from about 5 percent to about 50 percent of the total gas pressure of alpha olefin, carbon monoxide and hydrogen.

13. A process as defined in claim 3 wherein the non-reactive organic solvent which is a solvent for the complex catalyst is selected from the group consisting of 3-pentanone, 4-heptanone and the dimethyl ethers of tetraethylene glycol.

14. A hydrocarbonylation process for producing a mixture of a ketone and an aldehyde which comprises:
   (I) forming a reaction mixture comprising:
      (a) a catalytic amount of complex catalyst consisting essentially of rhodium in complex combination with
         (i) a triarylphosphine, and
         (ii) p-nitrobenzoic acid,
      (b) an alpha-olefin having 2 to 4 carbon atoms,
      (c) carbon monoxide, and
      (d) hydrogen,
      with the proviso that the reaction mixture has a mole ratio of said p-nitrobenzoic acid to rhodium of at least about 7; and the further proviso that the mole ratio of trisrylphosphine to rhodium present in the reaction mixture is not in excess of about 3;
   (II) maintaining the reaction mixture at a temperature of from about 50° C. to about 200° C. and a total pressure of alpha-olefin, carbon monoxide and hydrogen of less than 525 psi wherein the partial pressure of carbon monoxide is from about 5% to about 50% of the total pressure of carbon monoxide, alpha-olefin and hydrogen, with the proviso that when the the partial pressure of carbon monoxide is from about 5% to about 20% of the total pressure of carbon monoxide, alpha-olefin and hydrogen, the ratio of the partial pressure of the alpha-olefin to hydrogen is from about 5/1 to about 1/5 and the further proviso that when the partial pressure of carbon monoxide is from about 21% to about 50% of the total pressure of carbon monoxide, alpha-olefin and hydrogen, the ratio of the partial pressure of alpha-olefin to hydrogen is from about 5/1 to about 2/1.

15. A process as defined in claim 14 wherein the alpha-olefin is ethylene or propylene.

16. A process as defined in claim 15 wherein the total pressure of alpha-olefin, carbon monoxide and hydrogen is from about 100 psi to about 300 psi.

17. A process as defined in claim 16 wherein the organic compound that is a solvent for (a), (b) and (c) is selected from the group consisting of 3-pentanone, 4-heptanone and the dimethyl ether of tetraethylene glycol.

* * * * *